US012582446B2

(12) United States Patent
Zander et al.

(10) Patent No.: US 12,582,446 B2
(45) Date of Patent: Mar. 24, 2026

(54) COLLAPSIBLE SURGICAL FASTENER

(71) Applicant: Stryker European Operations Limited, Carrigtwohill (IE)

(72) Inventors: Nils Zander, Eckernförde (DE); Manfred Wieland, Kiel (DE); Bernd Simon, Kiel (DE)

(73) Assignee: Stryker European Operations Limited, Carrigtwohill (IE)

( * ) Notice: Subject to any disclaimer, the term of this patent is extended or adjusted under 35 U.S.C. 154(b) by 422 days.

(21) Appl. No.: 18/096,852

(22) Filed: Jan. 13, 2023

(65) Prior Publication Data

US 2023/0218319 A1 Jul. 13, 2023

Related U.S. Application Data

(60) Provisional application No. 63/299,198, filed on Jan. 13, 2022.

(51) Int. Cl.
 *A61B 17/68* (2006.01)
 *A61B 17/56* (2006.01)
 *A61B 17/86* (2006.01)
(52) U.S. Cl.
 CPC .......... *A61B 17/683* (2013.01); *A61B 17/864* (2013.01); *A61B 2017/564* (2013.01)
(58) Field of Classification Search
 CPC ................ A61B 17/683; A61B 17/864; A61B 2017/564
 See application file for complete search history.

(56) References Cited

U.S. PATENT DOCUMENTS

| | | | |
|---|---|---|---|
| 8,114,141 B2 | 2/2012 | Appenzeller et al. | |
| 9,155,578 B2 | 10/2015 | Chegini et al. | |
| 2010/0268285 A1 | 10/2010 | Tipirneni et al. | |

FOREIGN PATENT DOCUMENTS

| | | | | |
|---|---|---|---|---|
| CN | 103445851 B | 9/2015 | | |
| EP | 0340413 A1 | 11/1989 | | |
| EP | 2074956 A1 * | 7/2009 | ........... | A61B 17/744 |
| GB | 1337688 A | 11/1973 | | |

(Continued)

OTHER PUBLICATIONS

McKoy, B.E. et al., "An expandable anchor for fixation in osteoporotic bone," Journal of Orthopaedic Research, Jul. 31, 2000, pp. 545-547, vol. 19, Elsevier.

(Continued)

*Primary Examiner* — Kevin T Truong
*Assistant Examiner* — Diana Jones
(74) *Attorney, Agent, or Firm* — Lerner David LLP

(57) ABSTRACT

A surgical fastener includes a cannulated collapsible fastening body having a trailing end and a leading end and defining a passage extending from the trailing end to the leading end, and a pin having a non-threaded shaft at least partially disposed within the passage and an enlarged tip. A method of using the surgical fastener includes engaging an end of a driver with a recess in a head of the surgical fastener, including inserting an extension at the end of the driver into the passage, and inserting the fastener into a bore in a bone during which the extension of the driver abuts a trailing end of the shaft of the pin to prevent the pin from moving in a direction from the leading end to the trailing end relative to the fastening body.

17 Claims, 5 Drawing Sheets

(56)        References Cited

FOREIGN PATENT DOCUMENTS

| WO | 2017147140 | A1 | 8/2017 |
| WO | 2019010252 | A2 | 1/2019 |
| WO | 2020146684 | A2 | 7/2020 |

OTHER PUBLICATIONS

Extended European Search Report including Written Opinion for Application No. 23151515.6 dated May 22, 23, pp. 1-7.

* cited by examiner

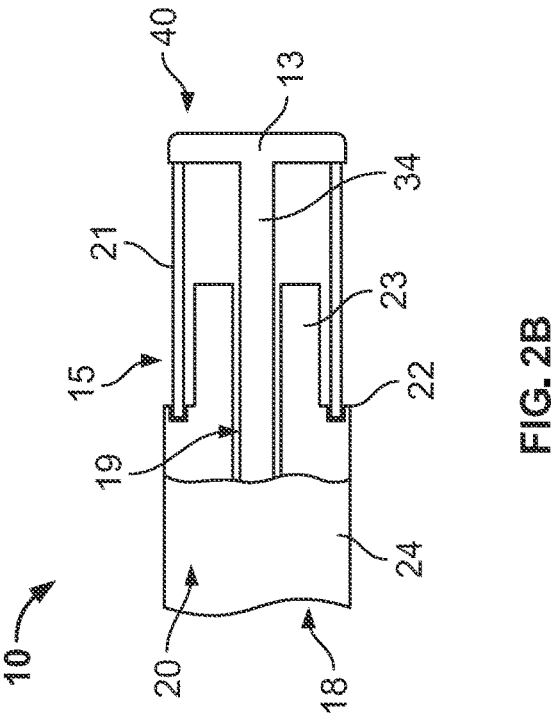
FIG. 2B
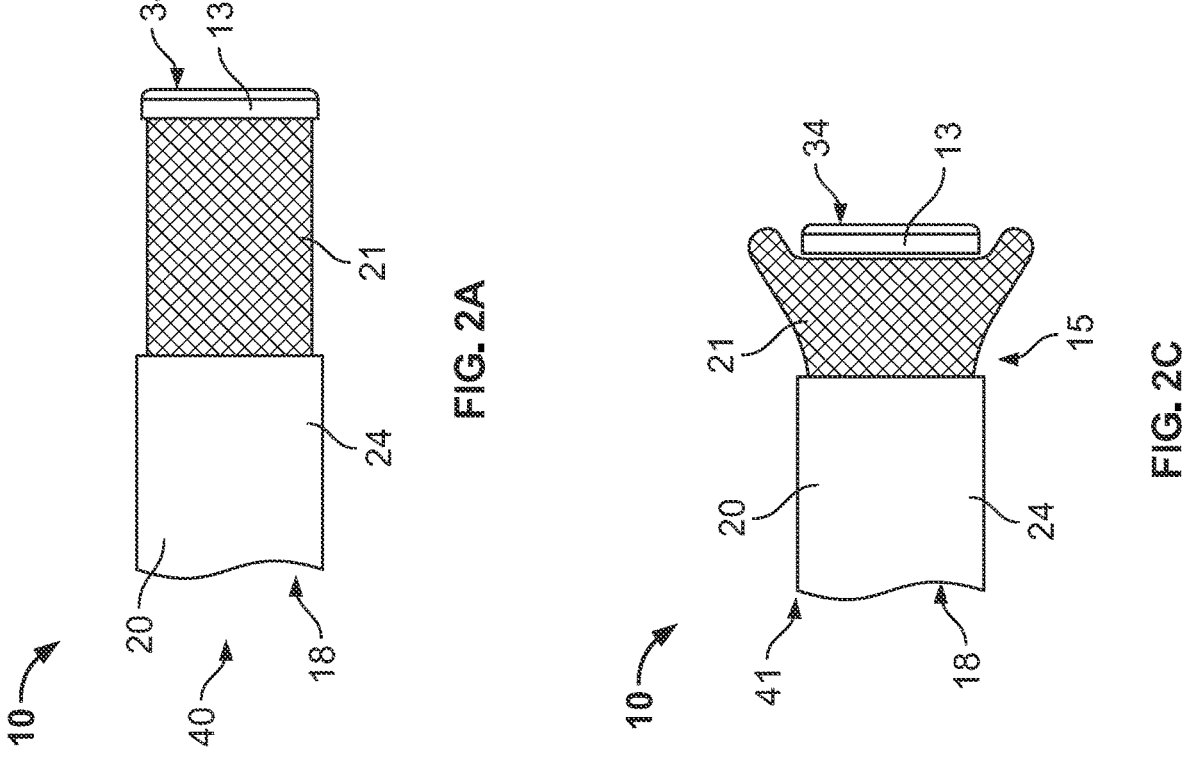
FIG. 2A
FIG. 2C

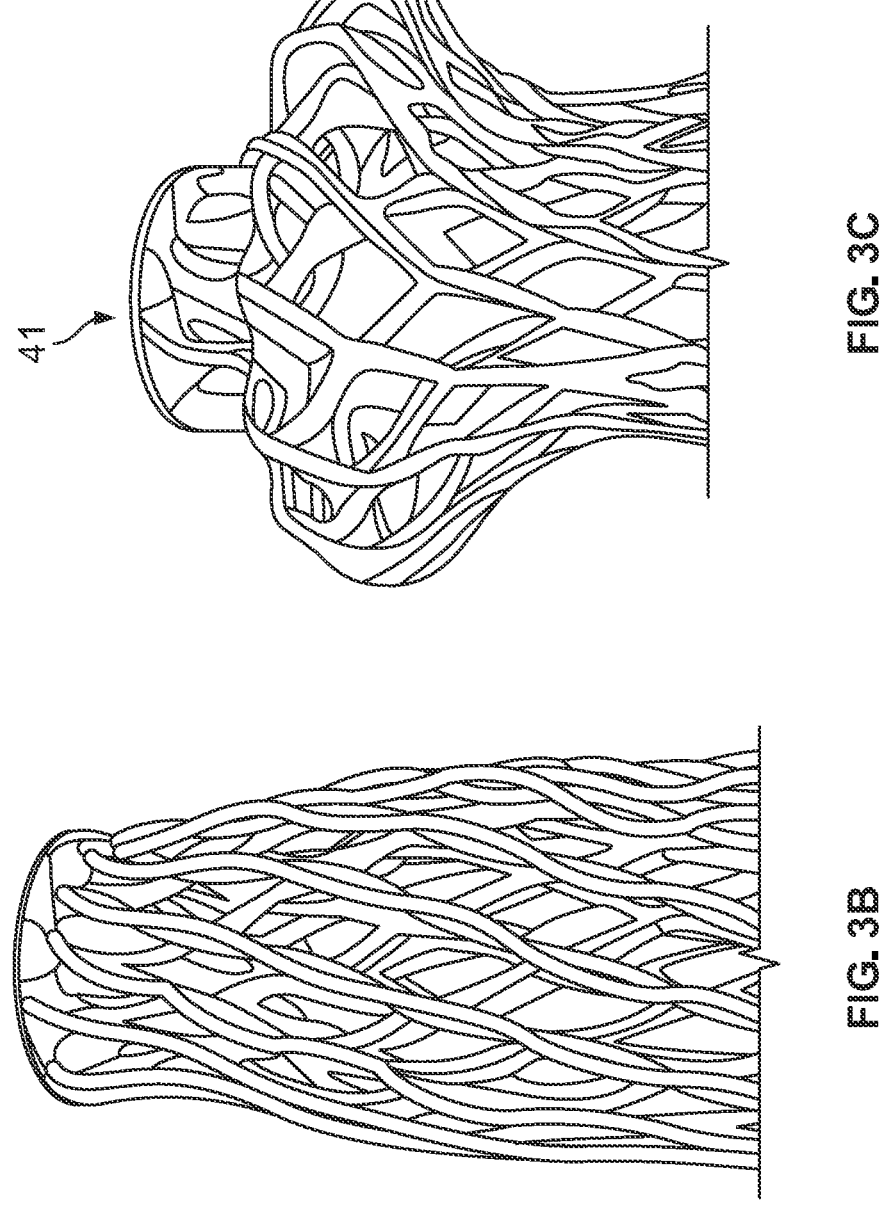
41
FIG. 3C
40
FIG. 3B
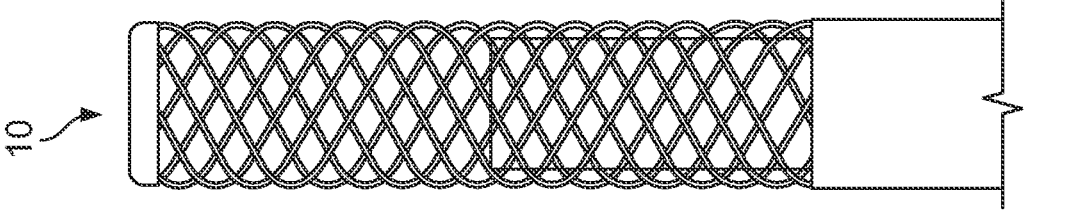
10
FIG. 3A

COLLAPSIBLE SURGICAL FASTENER

CROSS-REFERENCE TO RELATED APPLICATIONS

The present application claims the benefit of the filing date of U.S. Provisional Application No. 63/299,198, filed Jan. 13, 2022, the disclosure of which is hereby incorporated herein by reference.

BACKGROUND OF THE INVENTION

The surgical treatment of proximal humeral fractures remains challenging and is associated with significant clinical complications. Angularly stable lateral plating constructs are the treatment of choice for more complex fracture situations. However, these common constructs have various disadvantages, such as the incidence of secondary loss of fixation, varus mal-alignment of the head fragment, and subsequent (or even initial) cut-out or cut-through of proximal fixation screws. Complication rates associated with insufficient fixation remain rather high.

There is a need to address the root causes of these treatments, which are understood to be associated with instabilities of the medial collum (calcar), non-appropriate bony support, and voids within the humeral head and/or the inability of the screw tips to sufficiently anchor within the subchondral bone, while also effectively supporting the head fragment from rotation and/or distal translation.

BRIEF SUMMARY OF THE INVENTION

A first aspect of the present invention is a surgical fastener including a cannulated collapsible fastening body having a trailing end and a leading end and defining a passage extending from the trailing end to the leading end, and a pin having a non-threaded shaft at least partially disposed within the passage and an enlarged tip.

In accordance with other embodiments of the first aspect, the fastening body may include a head, a shaft portion, and a mesh portion. The shaft portion may have a threaded outer surface. An entire outer surface of the shaft portion may be non-threaded. The mesh portion may be fixedly attached to the shaft portion. The mesh portion may be fixedly attached to the tip of the pin. The mesh portion may be comprised of a flexible material, and in an actuated configuration of the surgical fastener, a portion of the mesh portion may be expanded outward from the passage. In the actuated configuration of the surgical fastener, the tip of the pin may contact the shaft portion of the fastening body.

The shaft portion may be comprised of a rigid material, and the mesh portion may be comprised of a mesh material that is more flexible than the rigid material. The mesh material may be a nickel-titanium alloy. The mesh material may be a polymer material. In a resting configuration of the surgical fastener, a maximum outer diameter of the shaft portion may be substantially similar to a maximum outer diameter of the mesh portion. In the resting configuration, values of the maximum outer diameter of the shaft portion and the maximum outer diameter of the mesh portion may each be 3 mm to 8 mm. The shaft portion may include a main section having the maximum outer diameter and a protrusion having an outer diameter less than the maximum outer diameter of the main section. The protrusion of the shaft portion may be disposed within the mesh portion. A length of the mesh portion may be greater than a length of the protrusion of the shaft portion. The mesh portion may be fixedly attached to a shoulder defined between the main section and the protrusion of the shaft portion.

The tip of the pin may have a maximum outer diameter greater than a maximum inner diameter of the passage. A kit may include the aforementioned surgical fastener, and a cortical bone plate including a hole for engaging with a head of the fastener. A kit may include the aforementioned surgical fastener, and an intramedullary nail.

A kit may include the aforementioned surgical fastener, and a driver having an end with a non-circular cross section for engagement with a recess in a head of the fastener, wherein the end of the driver includes an extension having a maximum outer diameter smaller than a maximum inner diameter of the passage and configured to be disposed within the passage to contact the shaft of the pin of the fastener. The kit may further include a second driver having an end with a non-circular cross section terminating in a planar surface for engagement with the recess in the head of the fastener.

A second aspect of the present invention is a method of using a surgical fastener, including engaging an end of a driver with a recess in a head of a surgical fastener, the fastener including a cannulated collapsible fastening body having a trailing end and a leading end and defining a passage extending from the trailing end to the leading end, and a pin having a shaft at least partially disposed within the passage and a tip, wherein the step of engaging includes inserting an extension at the end of the driver into the passage, and inserting the fastener into a bore in a bone during which the extension of the driver abuts a trailing end of the shaft of the pin to prevent the pin from moving in a direction from the leading end to the trailing end relative to the fastening body.

In accordance with other embodiments of the second aspect, the step of inserting may include inserting the fastener into a final implanted position within the bore of the bone. The shaft of the pin may be non-threaded to allow non-rotatable movement of the pin within the passage of the fastening body, and the fastening body may include a shaft portion comprised of a rigid material and a mesh portion comprised of a mesh material that is more flexible than the rigid material. After the fastener is inserted to the final implanted position, a portion of the passage adjacent the head may be unobstructed to permit movement of the pin within the passage during which a portion of the mesh portion is expanded outward from the passage and into the surrounding bone material. After the fastener is inserted to the final implanted position, a maximum outer diameter of the shaft portion may be substantially similar to a maximum outer diameter of the mesh portion.

The step of inserting may include partially inserting the fastener into the bore of the bone, and the method may further include removing the driver, engaging an end of a second driver with the recess in the head of the fastener, the end of the second driver having a non-circular cross section terminating in a planar surface, and further inserting the fastener into the bore in the bone into a final implanted position while allowing surrounding bone and/or tissue to collapse the fastening body. The shaft of the pin may be non-threaded to allow non-rotatable movement of the pin within the passage of the fastening body, and the fastening body may include a shaft portion comprised of a rigid material and a mesh portion comprised of a mesh material that is more flexible than the rigid material. During the step of further inserting, the method may include surrounding bone and/or tissue causing movement of the pin within the passage such that a portion of the mesh portion is expanded outward from the passage and into the surrounding bone material. During the step of partially inserting, a maximum outer diameter of the shaft portion may be substantially similar to a maximum outer diameter of the mesh portion.

The step of inserting may include inserting the fastener into a hole of a cortical bone plate. The step of inserting may include inserting the fastener into a hole of an intramedullary nail. The step of inserting may include rotating the shaft portion to engage a threaded outer surface thereof with the bone. The step of inserting may include non-rotatably advancing the fastening body into the bore.

A third aspect of the present invention is a method of using a surgical fastener, including selecting one of a passive driver and an active driver, the passive driver having an end with a non-circular cross section, wherein the end of the passive driver includes an extension having a maximum outer diameter smaller than a maximum outer diameter of the end with the non-circular cross section, the active driver having an end with a non-circular cross section terminating in a planar surface, engaging the end of the selected driver with a recess in a head of a surgical fastener, the fastener comprising a cannulated collapsible fastening body having a trailing end and a leading end and defining a passage extending from the trailing end to the leading end, and a pin having a shaft at least partially disposed within the passage and a tip, wherein when the passive driver is selected, the step of engaging further includes inserting the extension at the end of the passive driver into the passage, and inserting the fastener into a bore in a bone.

In accordance with other embodiments of the third aspect, when the passive driver is selected, the step of inserting may further include the extension of the driver abutting a trailing end of the shaft of the pin to prevent the pin from moving in a direction from the leading end to the trailing end relative to the fastening body.

BRIEF DESCRIPTION OF THE DRAWINGS

The drawings described herein are for illustrative purposes only of the selected embodiments and are not all possible implementations and thus are not intended to limit the scope of the present disclosure.

FIG. 2A illustrates a distal end of a surgical fastener of the present invention in a resting configuration.

FIG. 2B illustrates a cross-sectional view of the distal end of the surgical fastener of FIG. 2A.

FIG. 2C illustrates the distal end of the surgical fastener of FIG. 2A in an actuated configuration.

FIGS. 3A-C show the distal end of the surgical fastener of FIG. 2A prior to insertion, in its resting configuration, and in its actuated configuration, respectively.

DETAILED DESCRIPTION

Figure 1B:
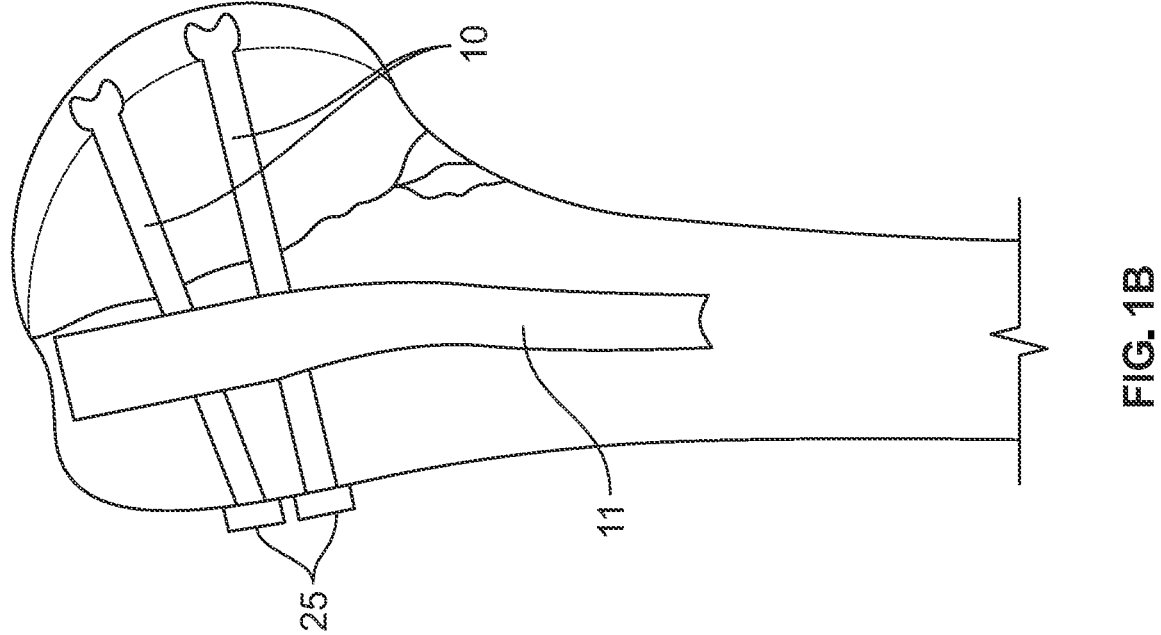
FIG. 1B illustrates a surgical fastener system including a surgical fastener in connection with an intramedullary nail, in accordance with another exemplary embodiment of the present invention.

In general, the present invention aims to improve the anchoring properties of current bone screws by introducing a surgical fastener with an expandable design comprising a rigid shaft portion and a deformable mesh portion, and specific drivers to be employed in the implantation process. As shown in FIGS. 1A-B, 2A-B, 3A-C, and 4C, a surgical fastener 10 is provided that includes a cannulated collapsible fastening body 18 and a pin 34 movable within the fastening body 18.

The fastening body 18 has a head 25, a shaft portion 20, and a mesh portion 21, and extends from a trailing end 14 to a leading end 15 with a passage 19 extending through the entire length of the fastening body 18 so that it is completely cannulated. The head 25 of the fastening body 18 has a non-circular cross-section, such as a hex head, so that it can be manipulated and rotated by a surgical tool such as pliers or a socket wrench. An outer surface of the shaft portion 20 is shown in FIGS. 2A-C as non-threaded. In various embodiments, the outer surface can be entirely threaded, entirely non-threaded, or partially threaded along only a portion of its length. Two or more distinct threaded portions can also be provided on the shaft portion 20.

Existing screws, bolts, and pegs can be modified and utilized as the fastening body 18. This includes both nailing indications, such as standard locking screws, advanced locking screws or dedicated pegs, and plating indications, such as angularly stable screws (either fixed or variable angle), cortical screws, and cancellous screws. This allows existing technology to be modified and repurposed to meet the novel design of the present fastening body 18. The size of the fastening body 18 can be tailored to the particular surgical procedure or the particular patient anatomy, and a variety of differently sized and shaped fastening bodies can be produced for selection by a user. Length, diameter, thread pitch, head type, proportional length of the fastening body to the pin 34, and other attributes can be varied among different fasteners. For example, diameters of the shaft portion 20 can range from approximately 3 mm to 8 mm.

The mesh portion 21 is located at a distal end of the fastening body 18, as shown in FIGS. 2A-C. The mesh portion 21 is comprised of a flexible mesh material that is more flexible than the rigid material of the shaft portion 20. A preferred material of the mesh portion is nickel-titanium alloy, though other similar materials can be utilized such as a polymer material that are flexible and constructed to revert to their originally-configured shape when at rest. Overall, the mesh portion 21 is intended to be manufactured from material with hyper-elastic properties to withstand the required deformations, as discussed below. While various materials can be used, the flexibility of the material of the mesh portion 21 should be greater than that of the fastening body 18, which is more rigid.

The mesh portion 21 is tubular and hollow so that it is disposed about the distal end of the shaft portion 20. FIGS. 2A-C show the mesh portion 21 of the surgical fastening body 18 attached to the shaft portion 20, and this attachment may be a fixed or non-removable attachment. More particularly, FIG. 2B shows that the shaft portion 20 includes a larger main section 24 with a maximum outer diameter greater than that of a smaller protrusion 23 of the fastening body that extends distally from the main section 24. The mesh portion 21 can be fixedly attached to a shoulder 22 defined between the main section 24 and the protrusion 23 and configured so that it extends over and has a greater length than the protrusion 23 when the mesh portion 21 is at rest. That is, the protrusion is disposed within the tubular configuration of the mesh portion 21 regardless of the configuration of the mesh portion 21. While shown fixed, the mesh portion can be inserted into a recess or otherwise held in a removable or non-fixed configuration with respect to fastening body 18.

The pin 34 of the surgical fastener 10 is a separate and distinct element from the fastening body 18 that is at least partially disposed within the passage 19 of the fastening body 18. The pin 34 has an enlarged tip 13 at its distal end and a shaft 35 extending proximally therefrom, and it is the shaft 35 in particular that disposed within the passage 19. The shaft 35 is shown in FIG. 2B as non-threaded so that it can slide axially and non-rotatably within the passage 19. In other embodiments, the shaft 35 may be partially or entirely threaded so that it rotates about its axis during axial movement within the passage 19. The tip 13 extends radially outward from the shaft 35 to a maximum outer diameter that is greater than a maximum inner diameter of the passage 19 so that only the shaft 35 of the pin 34 can move through the passage 19, which gives pin 34 a limit to the distance it can travel with respect to the shaft portion 20. As with the fastening body 18, the pin 34 should be made of a material that is more rigid and less flexible than the mesh portion 21 so that the mesh portion 21 can be actuated properly.

In the depicted embodiment, the mesh portion 21 of the fastening body 18 is also fixedly attached to the tip 13 of the pin 34. This provides a stable connection of the mesh body 21 to both the shaft portion 20 and the pin 34 with those two elements movable relative to one another, causing the mesh portion 21 to deform based on relative movement between the shaft portion 20 and the pin 34. In other embodiments, the mesh portion 21 can simply abut or be otherwise removably connected to the pin 34 to utilize a non-fixed connection. When the surgical fastener 10 is in a resting configuration as shown in FIGS. 2A and 2B, the mesh portion 21 is in a substantially cylindrical shape such that the maximum outer diameter of the mesh portion 21 is substantially similar to the maximum outer diameter of the shaft portion 20. This means that the outer surface of the entire surgical fastener 10 will be about the same from end to end, excluding the head 25. In this resting configuration, the maximum outer diameters of the shaft portion 20 and of the mesh portion 21 are each in the range of 3 mm to 8 mm, for example.

When the surgical fastener 10 is actuated, the pin 34 is moved within the passage in a direction toward the head 25 of the fastening body 18. This causes the mesh portion 21 to deform so that a portion thereof moves radially outward from the pin 34, as shown in FIG. 2C. In this actuated configuration of the surgical fastener 10, the mesh portion 21 is deformed or expanded outward from the passage 19 such that the tip 13 of the pin 34 moves closer to and may ultimately contact the shaft portion 20. To facilitate this operation, the material of the mesh portion 21 has hyperelastic properties to withstand the required deformations, as illustrated in FIGS. 1 and 2C.

Figure 1A:
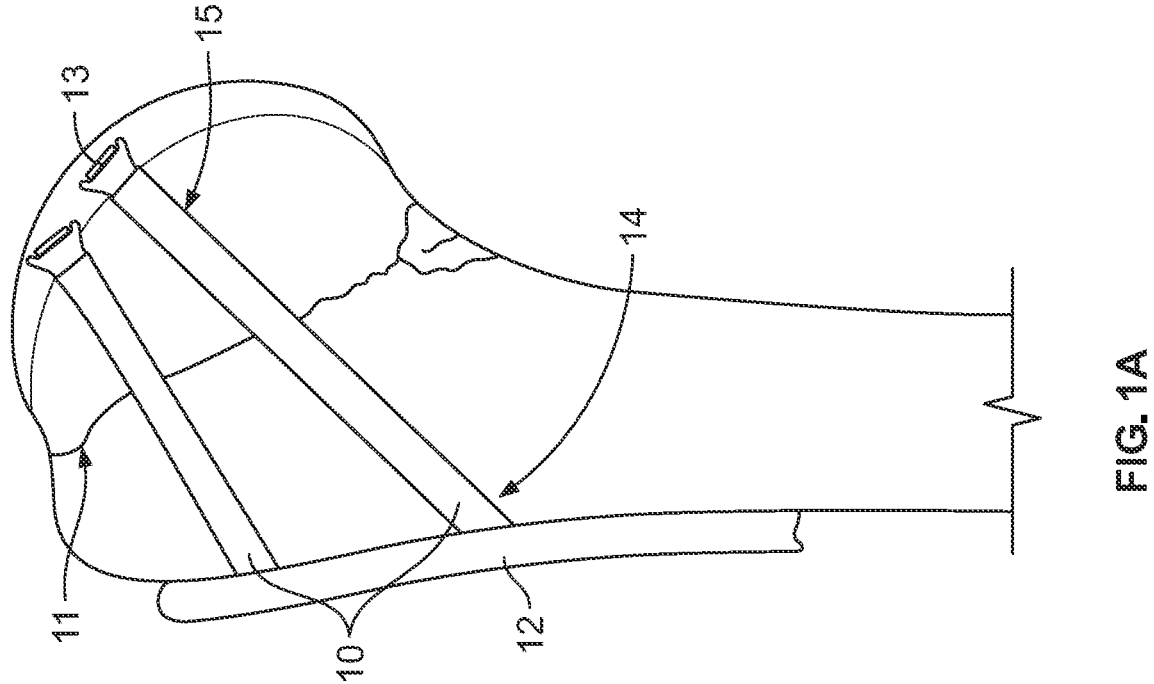
FIG. 1A illustrates a surgical fastener system including a surgical fastener in connection with a cortical bone plate, in accordance with an exemplary embodiment of the present invention.

As shown in FIG. 1A, the surgical fastener 10 can be utilized with a cortical bone plate 12 such that the head 25 engages a hole in the plate 12 after insertion. Also, or alternatively, the surgical fastener 10 can be used with an intramedullary nail 11, as shown in FIG. 1B. The fastener 10 can be disposed through a hole of the nail 11 or may be inserted in the same procedure as the nail 11 but not physically connected to it. Kits can be provided including one or more surgical fasteners 10, one or more cortical bone plates 12, and/or one or more intramedullary nails 11. Any one component can be provided in multiple different sizes and/or shapes.

Figure 4C:
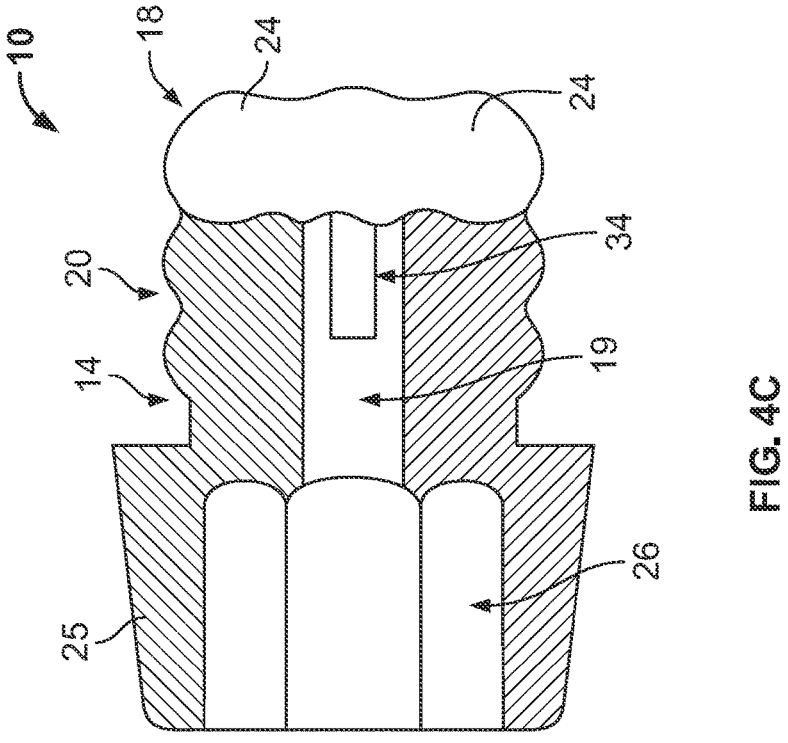
FIG. 4C illustrates a cross-sectional view of a proximal end of the surgical fastener of FIG. 2A.
Figure 4A:
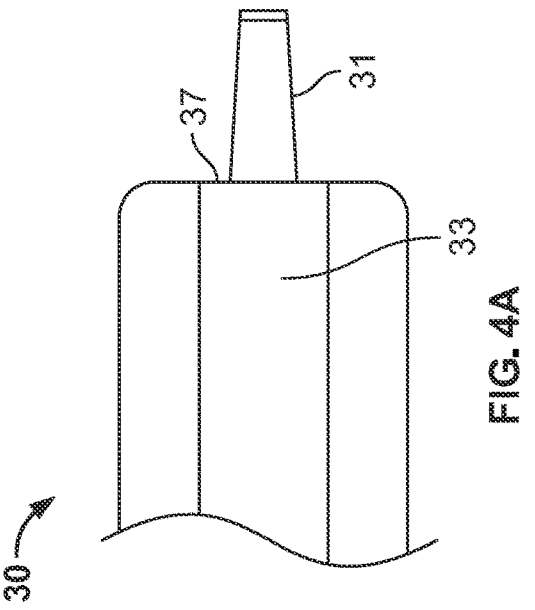
FIGS. 4A-B illustrate two drivers used in connection with the surgical fastener of FIG. 2A.

The surgical fastener 10 is configured to be inserted with different types of specialized drivers depending on the result to be achieved after its insertion. As shown in FIG. 4A, a passive driver 30 has an engagement end 33 with a non-circular cross section, such as a hex head, for engagement with a recess 26 in the head 25 of the fastener 10. Extending distally from a face 37, which may be flat, at the end of driver 30 is an extension 31 that is configured with a maximum outer diameter smaller than that of the end 33 of the driver 30. The maximum outer diameter of the extension 31 is also smaller than the maximum inner diameter of the passage 19 so that the extension 31 can be advanced into the passage 19 during use, and in particular to contact and/or prevent proximal movement of the shaft 34 of the pin 35.

Figure 4B:
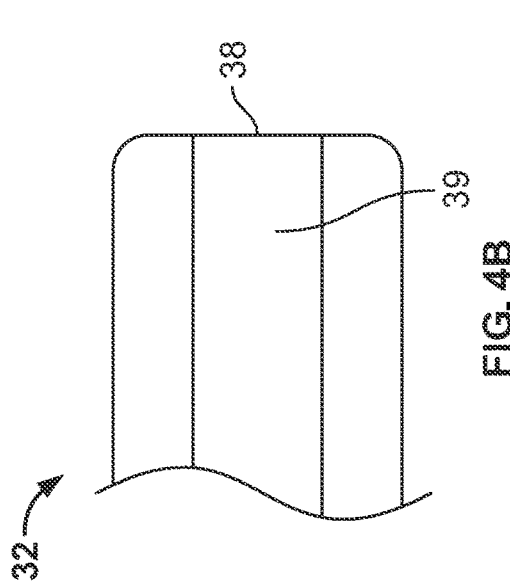

As shown in FIG. 4B, another type of driver is shown as an active driver 32 also having an end 39 with a non-circular cross section. This non-circular cross section terminates in a surface 38 that is preferably flat or planar and does not include any extension, in contrast to driver 30. This permits the non-circular cross-section of driver 32 to be engaged with the recess in the head 25 in the same manner as driver 30 but without having any portion that extends into the passage 19. It is preferable that both drivers 30 and 32 have the same size and shape of their non-circular cross sections at the engagement ends. The surgical fastener 10 can be packaged in a kit with one or both drivers 30 and 32 so that a user can determine the best method of use of the product and be equipped to use the full range of capabilities of the fastener 10.

Accordingly, a method of using the surgical fastener 10 involves engaging the end 33 of the passive driver 30 with the recess 26 in the head 25 of the surgical fastener 10 such that the extension 31 extends into the passage 19. In this way, the extension 31 is positioned to limit or prevent proximal movement of the pin 35 toward the trailing end 14 during insertion of the fastener 10, so that the mesh portion 21 remains in its resting cylindrical configuration. After a bore is drilled in the bone to the diameter of the shaft of the fastener 10, the passive driver 30 is used to insert the surgical fastener 10 into a bore in a bone in this cooperative configuration relative to the fastening body 18, which can result in the surgical fastener 10 being placed into its final implanted position while in its resting configuration. Since the shaft 35 of the pin 34 is non-threaded, non-rotatable axial movement of the pin 34 within the passage 19 toward the head 25 of the fastening body 18 is permitted after implantation. This can occur after the surgical fastener 10 is placed in its final implanted position, where during healing the pin 34 can migrate toward the trailing end 14 in the unobstructed passage 19, which also causes the mesh portion 21 to expand outward and into the surrounding bone material to enhance fixation and healing. As it is well known in the medical arts that pressure on a bone fracture facilitates and expedite healing, this permits the mesh portion 21 to increase fixation while healing continues.

In an alternative method, the surgical fastener 10 in its resting configuration can be partially inserted with the passive driver 30 to a desired depth that is not its final position in the same manner as described above. Then, the procedure can be continued with use of the active driver 32. After partial insertion, the passive driver 30 can be removed, and the end of the active driver 32 is engaged with the recess 26 in the head 25. Since the passage 19 that is located proximally of the pin 34 is unobstructed, further insertion of the surgical fastener 10 with the active driver 32 toward its final implanted position causes the surrounding bone and/or tissue to force the pin 34 to move toward the trailing end 14, collapsing the fastening body 18 by extending the mesh portion 21 outward. The proximal forces on the tip 13 of the pin 34 are greater than the forces required to deform the elastic material of the mesh portion 21 and press it into the surrounding bone material, which is typically cancellous. This fixes the surgical fastener 10 radially deeper into the bone tissue to promote healing in an active way. The use of the active driver 32 is an optional step to cause deformation of the mesh portion 21. Of course, as discussed above, the mesh portion 21 may be later deformed passively by fragment dislocation.

In either insertion method, the tip 13 is guided and controlled by the passage or canulation 19 of the fastening body 18. This allows adequate insertion of the fastener 10 and avoids unintended activation of the mesh portion 21. The movement distance of the tip 13 can be controlled by selection of an appropriate driver as described above.

During insertion, if the outer surface of the fastening body 18 is threaded, the selected driver can be used to cause rotation of the surgical fastener 10 to engage a threaded outer surface thereof with the bone. Alternatively, insertion can be done without rotating the fastening body 18. The surgical fastener 10 can also be inserted into a hole in a cortical bone plate and/or into a hole in or a location adjacent to an intramedullary nail, as indicated above.

One benefit of the surgical fastener 10 is that it can permit a user to determine at the outset of a procedure whether to actively or passively insert the fastener 10 according to either of these described methods. This can involve selecting one of the active driver 32 and the passive driver 30 for use as appropriate and at the appropriate time.

Figure 5:
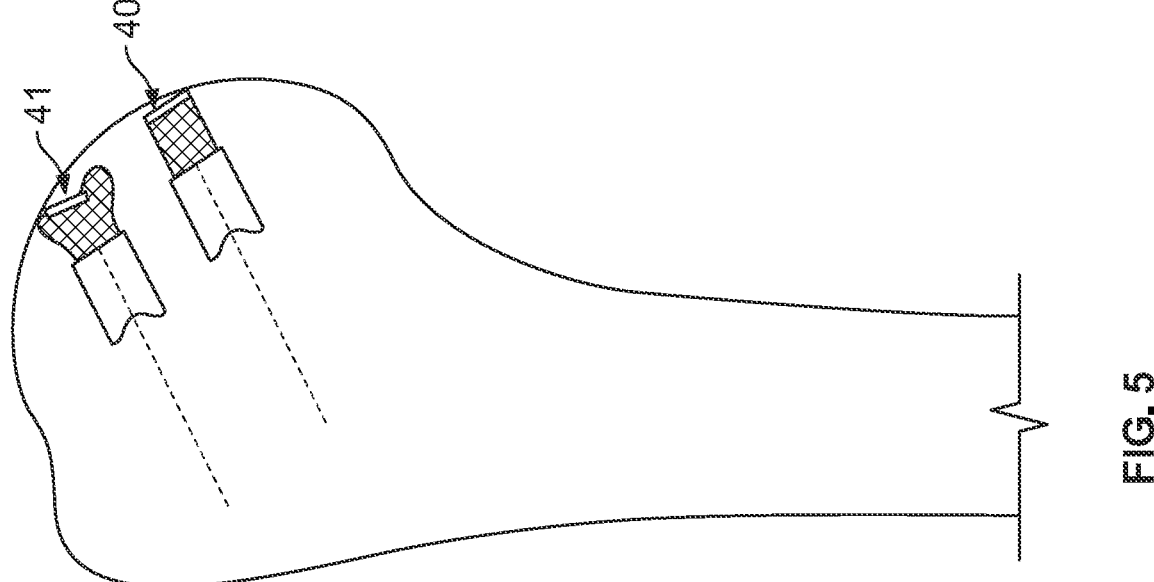
FIG. 5 illustrates implanted surgical fasteners of FIG. 2A in actuated and resting configurations.

FIG. 5 illustrates the final implanted positions for the surgical fastener 10 according to the above methods. When the fastener 10 is inserted into the final implanted position 40 based on use of passive driver 30, the maximum outer diameter of the shaft portion 20 is substantially similar to a maximum outer diameter of the mesh portion 21, as also shown in FIG. 3B. When the fastener 10 is inserted into the final implanted position 41 based on using the active driver 32, the maximum outer diameter of the mesh portion 21 is deformed to be substantially larger than the maximum outer diameter of the shaft portion 20, as also shown in FIG. 3C. In this final implanted position 41, a portion of the passage adjacent the head is unobstructed to permit movement of the pin 34 within the passage during which the mesh portion 21 is expanded outward from the passage and into the surrounding bone material. FIG. 3A additionally shows fastener 10 before insertion with its pin extended fully in the distal direction.

The present invention embodies a surgical fastener comprising a mechanical screw tip augmentation within the subchondral area of the proximal humerus by intended and controlled increase of the footprint resisting the translational forces of the humeral head fragment. The invention is a surgical fastener with a deformable tip design, which increases the cross-section or footprint when activated by axial forces applied onto the tip. This activation can generally happen passively by fragment dislocation or, in the alternative, actively by the user.

The shaft portion 20 and the pin 34 can each be made of any surgical grade rigid material such as plastic, ceramic, or metal, and particularly various metals such as titanium, titanium alloys, stainless steel, cobalt chrome alloys, tantalum and niobium, or any combination thereof. Gold and/or silver can be provided in the material composition or as a coating of a component. While certain materials have been described for the components of the fastener 10, it will be understood that the material selection should be made to facilitate the various uses of the components with respect to one another, namely, to permit deformation of the mesh portion 21.

Each component of the present invention may be formed by an additive manufacturing process, including but not limited to electron beam melting (EBM), selective laser sintering (SLS), selective laser melting (SLM), binder jet printing, and blown powder fusion for use with metal powders. In one embodiment, the fastener 10 can be manufactured by 3D printing such that the fastening body 18, the mesh portion 21, and the pin 34 are each connected together. The contouring of the mesh portion 21 and its relatively thinner design can permit flexing of the mesh portion 21 even when it is made of the same material as the fastening body 18 and the pin 34. Fixed connections between the elements can be made, particularly of the mesh portion 21 with the fastening body 18 and the pin 34. The fastening body 18 and the pin 34 may also be initially connected through a frangible connection that can be broken to facilitate relative movement between the fastening body 18 and the pin 34.

The present invention has been described for use with a humeral bone, although this is not an exclusive use of the present technology. Use of the present fastener 10 in any bone, such as the femur, tibia, etc. can provide the same benefits described above when deployed to enhance fixation of a bone fracture.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A surgical fastener comprising:
   a cannulated collapsible fastening body having a trailing end and a leading end and defining a passage extending from the trailing end to the leading end, wherein the fastening body includes a head, a shaft portion, and a mesh portion; and
   a pin having an enlarged tip and a non-threaded shaft, the non-threaded shaft at least partially disposed within the passage,
   wherein in a resting configuration of the surgical fastener, a maximum outer diameter of the shaft portion is substantially similar to a maximum outer diameter of the mesh portion, and
   wherein in the resting configuration of the surgical fastener, a portion of the passage located proximally of the pin is unobstructed to permit movement of the pin within the passage.

2. The surgical fastener of claim 1, wherein the shaft portion has a threaded outer surface.

3. The surgical fastener of claim 1, wherein an entire outer surface of the shaft portion is non-threaded.

4. The surgical fastener of claim 1, wherein the mesh portion is fixedly attached to the shaft portion.

5. The surgical fastener of claim 4, wherein the mesh portion is fixedly attached to the enlarged tip of the pin.

6. The surgical fastener of claim 1, wherein the mesh portion is comprised of a flexible material, and wherein in an actuated configuration of the surgical fastener, a portion of the mesh portion is expanded outward from the passage.

7. The surgical fastener of claim 6, wherein in the actuated configuration of the surgical fastener, the enlarged tip of the pin contacts the shaft portion of the fastening body.

8. The surgical fastener of claim 1, wherein the shaft portion is comprised of a rigid material, and the mesh portion is comprised of a mesh material that is more flexible than the rigid material.

9. The surgical fastener of claim 8, wherein the mesh material is a nickel-titanium alloy or a polymer material.

10. The surgical fastener of claim 1, wherein the shaft portion includes a main section having the maximum outer diameter and a protrusion having an outer diameter less than the maximum outer diameter of the main section.

11. The surgical fastener of claim 10, wherein the protrusion of the shaft portion is disposed within the mesh portion.

12. The surgical fastener of claim 1, wherein the enlarged tip of the pin has a maximum outer diameter greater than a maximum inner diameter of the passage.

13. A kit comprising:
the surgical fastener of claim 1; and
an intramedullary nail or a cortical bone plate comprising a hole for engaging with the head of the fastener.

14. A method of using a surgical fastener, comprising:
engaging an end of a driver with a recess in a head of a surgical fastener, the fastener comprising a cannulated collapsible fastening body having a trailing end and a leading end and defining a passage extending from the trailing end to the leading end, and a pin having a non-threaded shaft at least partially disposed within the passage and an enlarged tip, wherein the fastening body includes a shaft portion and a mesh portion, and wherein the step of engaging includes inserting an extension at the end of the driver into the passage; and
inserting the fastener into a bore in a bone during which the extension of the driver abuts a trailing end of the shaft of the pin to prevent the pin from moving in a direction from the leading end to the trailing end relative to the fastening body,
wherein in a resting configuration of the surgical fastener, a maximum outer diameter of the shaft portion is substantially similar to a maximum outer diameter of the mesh portion, and
wherein in the resting configuration of the surgical fastener, a portion of the passage located proximally of the pin is unobstructed to permit movement of the pin within the passage.

15. The method of claim 14, wherein the step of inserting includes partially inserting the fastener into the bore of the bone, and further comprising:
removing the driver;
engaging an end of a second driver with the recess in the head of the fastener, the end of the second driver having a non-circular cross section terminating in a planar surface; and
further inserting the fastener into the bore in the bone into a final implanted position while allowing surrounding bone and/or tissue to collapse the fastening body.

16. A method of using a surgical fastener, comprising:
selecting one of a passive driver and an active driver, the passive driver having an end with a non-circular cross section, wherein the end of the passive driver includes an extension having a maximum outer diameter smaller than a maximum outer diameter of the end with the non-circular cross section, the active driver having an end with a non-circular cross section terminating in a planar surface;
engaging the end of the selected driver with a recess in a head of a surgical fastener, the fastener comprising a cannulated collapsible fastening body having a trailing end and a leading end and defining a passage extending from the trailing end to the leading end, and a pin having a non-threaded shaft at least partially disposed within the passage and an enlarged tip, wherein the fastening body includes a shaft portion and a mesh portion, and wherein when the passive driver is selected, the step of engaging further includes inserting the extension at the end of the passive driver into the passage; and
inserting the fastener into a bore in a bone,
wherein in a resting configuration of the surgical fastener, a maximum outer diameter of the shaft portion is substantially similar to a maximum outer diameter of the mesh portion, and
wherein in the resting configuration of the surgical fastener, a portion of the passage located proximally of the pin is unobstructed to permit movement of the pin within the passage.

17. The method of claim 16, wherein when the passive driver is selected, the step of inserting further includes the extension of the driver abutting a trailing end of the shaft of the pin to prevent the pin from moving in a direction from the leading end to the trailing end relative to the fastening body.

* * * * *